United States Patent [19]
Tarr et al.

[11] Patent Number: 5,654,824
[45] Date of Patent: Aug. 5, 1997

[54] PORTABLE SELF-CLEANING MIRROR APPARATUS AND METHOD

[76] Inventors: Stephen E. Tarr, 2508 W. 12th, #303, Austin, Tex. 78703; D. Edward Tarr, 9513 S. Lakewood Ave., Tulsa, Okla. 74137

[21] Appl. No.: 507,589

[22] Filed: Jul. 26, 1995

[51] Int. Cl.⁶ .................... G02B 5/08; G02B 7/182; A47L 1/00; B60S 1/02
[52] U.S. Cl. .......... 359/507; 359/508; 359/872; 359/882; 359/900; 15/250.003; 433/30; 433/31
[58] Field of Search .................. 359/507, 508, 359/509, 872, 882, 900; 15/250.001, 250.003; 433/30, 31

[56] References Cited

U.S. PATENT DOCUMENTS

| | | | |
|---|---|---|---|
| 546,195 | 9/1895 | Sharp | 359/882 |
| 1,452,018 | 4/1923 | Allen . | |
| 2,608,708 | 9/1952 | Williamson . | |
| 2,722,707 | 11/1955 | Musselman . | |
| 2,809,430 | 10/1957 | Barber . | |
| 2,814,823 | 12/1957 | Werner . | |
| 2,948,912 | 8/1960 | Wisdom | 359/508 |
| 2,973,541 | 3/1961 | Beck . | |
| 3,447,187 | 6/1969 | Barrett | 15/250.003 |
| 3,539,247 | 11/1970 | Broussard . | |
| 3,829,199 | 8/1974 | Brown | 359/882 |
| 3,859,987 | 1/1975 | Holstad . | |
| 4,057,870 | 11/1977 | Priesemuth | 15/250.03 |
| 4,261,637 | 4/1981 | King | 359/508 |
| 4,327,457 | 5/1982 | Lunsford | 15/250.03 |
| 4,408,991 | 10/1983 | Engel . | |
| 5,093,748 | 3/1992 | Higdon . | |

FOREIGN PATENT DOCUMENTS

| | | | |
|---|---|---|---|
| 0687620 | 6/1964 | Canada | 359/508 |

*Primary Examiner*—Ricky D. Shafer
*Attorney, Agent, or Firm*—Shaffer & Culbertson; J. Nevin Shaffer, Jr.

[57] ABSTRACT

A portable self-cleaning mirror having a disposable housing within which is located the rotatable reflective surface. A removably attachable reusable motor is combined to provide power to rotate the reflective surface/mirror. The reflective surface is rotated beneath a wiper blade attachment bar with a wiper blade that bisects the reflective surface along a diameter. In one embodiment, the wiper blade is formed in an inverted "Y" shape so that the two branches of the "Y" contact the reflective surface and clean the surface with a leading and trailing contact motion. Additionally, the attachment bar is formed in a sinuous non-linear shape so that a more effective cleansing of the reflective surface is accomplished.

4 Claims, 2 Drawing Sheets

PORTABLE SELF-CLEANING MIRROR APPARATUS AND METHOD

BACKGROUND OF THE INVENTION

This invention relates to an improved portable self-cleaning mirror apparatus and method.

Both manual and automatically driven reflective surfaces have been known in the art for quite some time. For example, hand-held mirrors made of a variety of reflective surfaces have been known since the earliest times and automatically driven mirrors, such as rear view mirrors on automobiles, are ordinary. These mirrors can be cleaned by cloth or sponge infrequently and as needed. Additionally there are known in the art much smaller more delicate mirrors that are used in the dental business which require frequent cleaning. A number of solutions have been attempted to solve the problem of keeping a dental mirror clean and operable throughout the course of dental treatment. For example, the Engel Patent, U.S. Pat. No. 4,408,991, utilizes water as the force to rotate a mirror so that centrifugal force causes water and other "flowable" material to be thrown from the surface. The King Patent, U.S. Pat. No. 4,261,637, uses an "electromagnetically driven motor" to rotate the mirror for the same purpose as the Engel Patent. Other solutions have been tried, such as the Holstad Patent, U.S. Pat. No. 3,859,987, which utilizes air directed from underneath the mirror to keep the material from coating the mirror and the Broussard Patent, U.S. Pat. No. 3,539,247, which utilizes a roll of reflective film that is simply rolled from one side to the other as the film becomes dirty. Finally, there is known in the art mechanical means, such as set forth in the Beck Patent, U.S. Pat. No. 2,973,541, which utilizes a mechanically operated blade, much like a hand operated windshield wiper, to clean the surface of the mirror as needed. A substantially motorized version of this idea is set forth in the Wisdom Patent, U.S. Pat. No. 2,948,912, which is connected by wires to an electrical source in the handle which is used to rotate a mirror beneath a wiper that extends from one side to the center of the mirror and no further.

In spite of these improvements, there still exists a need in the industry for a portable mirror that is self-cleaning and hygienic. In today's society, the introduction of possible deadly diseases into a persons' mouth during the process of attempting to help a person is no help at all. As a result, there is a need in the art for providing a mirror which is portable, disposable, and self-cleaning. It, therefore, is an object of this invention to provide an improved portable, self-cleaning mirror, wherein the housing that is introduced to the patient's mouth is disposable and whereby an independent portable motor is removably attachable to subsequent disposable housings.

SHORT STATEMENT OF THE INVENTION

Accordingly, the portable self-cleaning mirror of the present invention includes a disposable headpiece with a movable mirror. Attached to the headpiece is a device for cleaning the mirror and associated with the disposable headpiece is a reusable removably attachable mechanism for rotating the mirror. In the preferred embodiment, the disposable headpiece includes a housing in which the moveable mirror is free to move. Additionally, an interconnecting device is free to move within the housing and connects the motor portion with the mirror while being contained within the housing. Still further, in a preferred embodiment of this invention a wiper blade is attached to the headpiece so that the wiper blade bisects the mirror and contacts the mirror across the diameter. In a preferred embodiment the wiper blade is a "Y" shaped blade which is inverted so that the two branches of the "Y" come into contact with the mirror's surface. Further, in another embodiment, a rigid wiper blade attachment bar is connected to the housing and shaped so as to cause an attached wiper blade to curve back and forth across the mirror's surface.

The method of invention includes the steps of constructing a disposable headpiece in the form of a housing within which a moveable reflective surface/mirror is free to move. The mirror is then connected to a power transmitting connector which takes the power from a motor, or other means of rotating the mirrors, and transfers it to the mirror thereby causing the mirror to rotate. A "Y" shaped wiper blade is then attached so as to contact the mirror's surface so that the two branches of the "Y" separately contact the mirror's surface and create a leading and trailing contact with the mirror's surface. Once the dental mirror of the present invention has been used, the housing, including the rotatable mirror and the connecting device are disposed of and a sterile new housing with mirror and connector are connected to the reusable removably attachable motor. By this method, a portable self-cleaning mirror that is completely sterile and from which no infectious disease may be transmitted is provided.

BRIEF DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE PREFERRED EMBODIMENT

Figure 1:
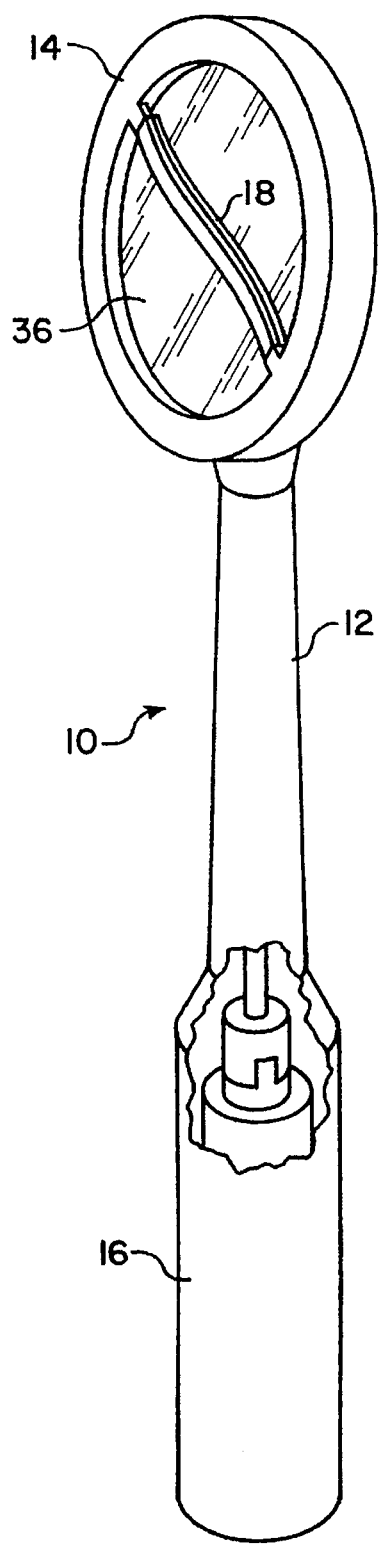
FIG. 1 is a plan view of a preferred embodiment of the portable self-cleaning mirror of the present invention with the housing shown in outline form to reveal the interior working parts.

The preferred embodiment of the present invention is illustrated by way of example in FIGS. 1–4. With specific reference to FIGS. 1 and 2, a portable self-cleaning mirror 10 includes a disposable housing 12 with a headpiece 14 and handpiece 16. Attached to headpiece 14 is wiper blade 18.

Figure 2:
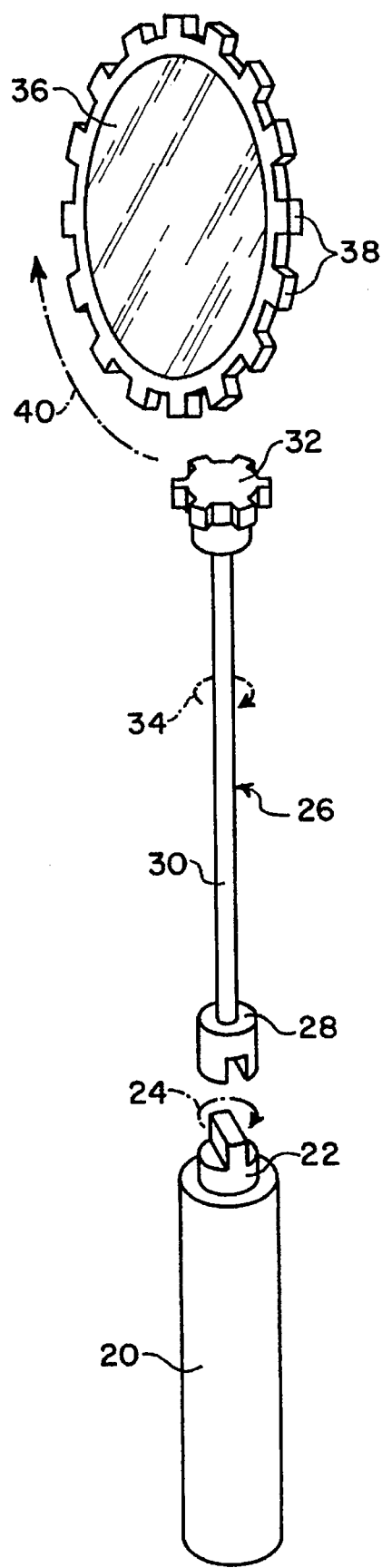
FIG. 2 is an exploded view showing the internal parts alone and their motion relative to each other.

Referring now to FIG. 2 handpiece 16 is formed so as to receive removably attachable reusable motor 20. Reusable motor 20 has a power take-off 22 rotating in the direction of arrows 24. Interconnector 26 has one end 28, elongated central section 30, and mirror engaging end 32. When end 28 is engaged with power take-off 22, interconnector 26 will rotate in the direction of arrows 34, the same direction as arrows 24.

Reflective surface 36 has at least one and preferably a number of engagement sections 38 located, in a preferred embodiment, around the perimeter of circular reflective surface 36. When mirror engaging end 32 of interconnector 26 engages engagement sections 38 and motor 20 is operated, reflective surface 36 will be rotated in the direction of arrows 40. In another embodiment reflective surface 36 is attached to a separate gear (not shown) with engagement sections 38.

Figure 3:
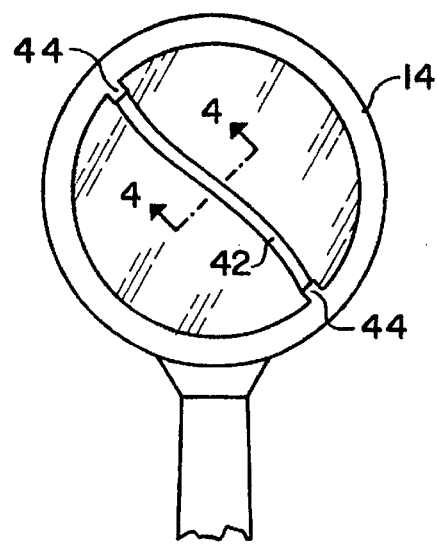
FIG. 3 is a top view of a part of the housing that holds the rotatable reflective mirror surface.

Referring now to FIG. 3, a top view of the headpiece 14 is shown with a wiper blade attachment bar 42 attached to opposite sides of headpiece 14 at connections 44 so that wiper blade attachment bar 42 substantially transverses the diameter of the headpiece 14. Further, wiper blade attachment bar is formed so as to result in a sinuous, more or less "S" shape from side to side of headpiece 14.

Figure 4:
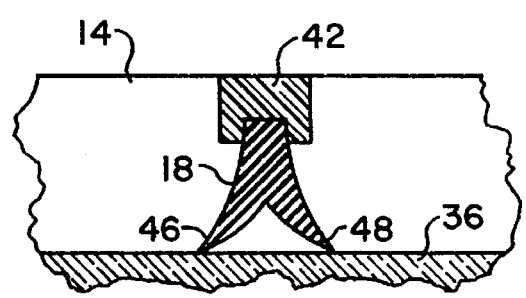
FIG. 4 is a side sectional view of FIG. 3 along line 4—4 showing a preferred embodiment of a wiper blade to be attached.

Referring now to FIG. 4, a side sectional view of headpiece 14 is shown with connections 44. Also shown is a side section view of wiper blade 18. In a preferred embodiment, wiper blade 18 is shaped in a "Y" form with branches 46 and 48 inverted so as to come into contact with the surface of reflective surface 36 thereby forming leading and trailing contacts.

In operation, disposable housing 12 is formed by any means and method known in the art such as two "clamshell" pieces and reflective surface 36 is formed so as to conform to the dimensions of headpiece 14 so as to be able to move or rotate within headpiece 14. Interconnector 26 is also formed so as to fit within disposable housing 12 with mirror engaging end 32 movingly coupled with engagement sections 38 of reflective surface 36. Elongated central section 30 can be of any dimension desired so that the portable self-cleaning mirror 10 of the invention can be of any length that is desired.

Removably attachable reusable motor 20, in a preferred embodiment, is a battery operated motor that provides power to power take-off 22. The motor 20 could be a manual device as well. Motor 20 is the only part of portable self-cleaning mirror 10 that is reused. This is possible because no possible source of infection is possible to contact motor 20 since it is completely shielded within disposable housing 12 which, as its name implies, once a procedure is completed is totally disposed of in a sanitary safe way. That is, when the use of the portable self-cleaning mirror 10 is completed, disposable housing 12 including headpiece 14, handpiece 16, wiper blade 18 and interconnector 26 are all disposed of in a single piece. The only part remaining for reuse is motor 20.

The key to the successful operation of portable self-cleaning mirror 10, certainly, is the operation of wiper blade 18. Wiper blade 18 is attached to wiper blade attachment bar 42, which in a preferred embodiment is a rigid plastic or any other suitable substance, attached across the complete diameter of headpiece 14. The preferred inverted "Y" shape of wiper blade is utilized to contact the surface of the reflective surface 36 with leading and trailing contact points. Because the wiper blade is fixed across the entire diameter of the mirror 36 it takes but a single rotation of the mirror 36 to clean the entire surface. This is important for several reasons, one being that the rapid cleaning of the entire surface diminishes the drain on the reusable motor 20 so that the motor is capable of lasting an entire procedure. Additionally, it is important that material that obstructs a user's view be removed quickly during dental or other procedures. An additional component of portable self-cleaning mirror 10 and attachment bar 42 is that the attachment bar 42 is formed in a sinuous, non-linear, shape so that materials, some of which are hard and difficult to remove, may be easily picked up by wiper blade 18. The inventors have found that a straight line or linear wiper blade has less of an ability to scrape materials than a blade that is non-linearly formed. Further, the inventors have found that this sinuous shape greatly aides in moving deposited material off of the reflective surface 36 rather than allowing it to build up in front of the wiper blade 18 as in prior art straight blades.

While the present invention has been disclosed in connection with a portable self-cleaning mirror, particularly for use in dental services, it should be appreciated that the portable self-cleaning mirror can be used in other situations and services as well. The present invention provides an improved self-cleaning mirror that can easily be manipulated and is sanitary, because of its disposability, for use in other medical and personal hygiene situations as well.

While the present invention has been disclosed in connection with the preferred embodiment thereof, it should be understood that there may be other embodiments which fall within the spirit and scope of the invention as defined by the following claims.

I claim:

1. A portable self-cleaning mirror comprising:

(a) a separate disposable housing with a headpiece section with a moveable mirror;

(b) a means for cleaning the mirror comprising a wiper blade attached to the headpiece so that the wiper blade bisects the mirror in an "S" shape and contacts the mirror in a non-linear manner; and (c) a reusable means for moving said mirror conformed to be repeatedly, removeably attached to the separate, disposable housing so that once used, the separate, disposable housing, mirror and means for cleaning the mirror are disposed of and the means for moving the mirror is reused.

2. A portable self-cleaning mirror comprising:

(a) a separate disposable housing with a headpiece section with a moveable mirror;

(b) a means for cleaning the mirror comprising a wiper blade attached to the headpiece so that the wiper blade bisects the mirror in an "S" shape and contacts the mirror in a non-linear manner;

(c) a reusable means for moving said mirror conformed to be repeatedly, removeably attached to the separate, disposable housing so that once used, the separate, disposable housing, mirror and means for cleaning the mirror are disposed of and the means for moving the mirror is reused; and (d) the wiper blade is "Y" shaped and inverted so that both branches of the "Y" individually contact the mirror's surface, thereby forming leading and trailing contact points.

3. A two-piece portable self-cleaning mirror comprising:

(a) a disposable housing within which a rotatable reflective surface is free to rotate;

(b) a plurality of engagement teeth around the rotatable reflective surface;

(c) a two-ended connector connected at one end with the engagement teeth and at the other end with a removably attachable power take-off;

(d) the removably attachable power take-off connected to a power means for providing power to rotate the reflective surface; and (e) a "Y" shaped wiper blade inverted so that both branches of the "Y" contact the reflective surface and cleans the surface as it is rotated beneath the wiper blade.

4. A method of proving a two-piece portable self-cleaning mirror comprising the steps of:

(a) constructing a disposable housing within which a rotatable reflective surface is located so that it is free to rotate;

(b) forming the rotatable reflective surface with a plurality of engagement teeth around its outer perimeter;

(c) connecting one end of a two-ended connector with engagement teeth and the other end with a removably attachable power take-off;

(d) connecting the removably attachable power take-off to a power means for providing power to rotate the reflective surface;

(e) constructing a wiper blade with a "Y" shape and inverting the wiper blade so that both branches of the "Y" contact the reflective surface; and (f) operating the power means so that the reflective surface is cleaned by the wiper blade as the reflective surface is rotated beneath the wiper blade.

* * * * *